United States Patent [19]

Witzel et al.

[11] Patent Number: 4,814,501

[45] Date of Patent: Mar. 21, 1989

[54] PROCESS FOR PREPARING N,N-DIMETHYL 2-(METHYLTHIO) BENZAMIDES AND ANALOGS

[75] Inventors: Bruce E. Witzel, Westfield; Robert K. Baker, Cranford; Philippe L. Durette, New Providence; Robert A. Frankshun, Kenilworth, all of N.J.

[73] Assignee: Merck & Co., Inc., Rahway, N.J.

[21] Appl. No.: 138,251

[22] Filed: Dec. 28, 1987

[51] Int. Cl.$^4$ .................. C07C 149/41; C07C 102/06; C07D 213/62

[52] U.S. Cl. .................... 564/162; 564/134; 546/298

[58] Field of Search ................. 564/134, 162; 546/298

[56] References Cited

U.S. PATENT DOCUMENTS

| | | | |
|---|---|---|---|
| 3,530,181 | 9/1970 | Soloway et al. | 564/162 |
| 3,829,488 | 8/1974 | Wolf et al. | 564/162 |
| 3,878,225 | 4/1975 | Allen et al. | 260/326.12 R |
| 3,980,659 | 9/1976 | Fleckenstein et al. | 546/298 |

FOREIGN PATENT DOCUMENTS 26000 4/1981 European Pat. Off. .
1260868 1/1972 United Kingdom .

OTHER PUBLICATIONS

Newman, M. S. and Karnes, H. A., *J. Org. Chem.*, 31, 3980 (1966).
Muchowski, J. M., et al. *J. Med. Chem.*, 28, (8), 1037 (1985).
Carral, C. et al, Synthesis 172 (1984).

*Primary Examiner*—Paul Lieberman
*Assistant Examiner*—Helene Kirschner
*Attorney, Agent, or Firm*—Joseph F. DiPrima; Michael C. Sudol; Mario A. Monaco

[57] ABSTRACT

Pyrolysis of substituted salicylate O(N,N-dialkyl)thiocarbamates yielded the corresponding N,N-dialkyl-2-(methylthio)benzamide. Similarly, substituted 6-azasalicylate O(N,N-dialkyl)thiocarbamates yielded the corresponding N,N-dialkyl-2-(methylthio)-6-aza-benzamide.

3 Claims, No Drawings

PROCESS FOR PREPARING N,N-DIMETHYL 2-(METHYLTHIO) BENZAMIDES AND ANALOGS

BACKGROUND OF THE INVENTION

The conversion of phenols to thiophenols, for example, the phenol group contained in salicylates, has been successfully carried out by the following scheme, for example,

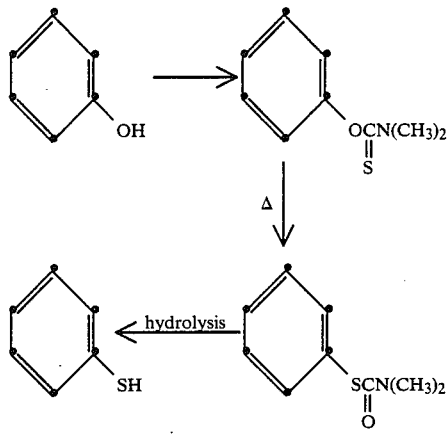

Various aromatic or heteroaromatic thiophenols have been synthesized by this method. Yields of the expected product are generally good, and few limitations have been placed on the substitution of the starting phenol. See Newman, M. S. et al., *J. Org. Chem.*, 31, 3980 (1966); Imada, I. et al., European Patent Application No. 26,000 (1981); Allen, R. C. et al., U.S. Pat. No. 3,878,225 (1975); and Carral, C. et al., *Synthesis*, 172(1984).

However, during the preparation of certain substituted thiosalicylic acids, we discovered, unexpectedly, that various substituted methyl salicylate N,N-dialkylthiocarbamates undergo a novel rearrangement to give the N,N-dialkyl 2-(methylthio)benzamides rather than the expected thiosalicylates. It happens that benzamides are useful intermediates for the preparation of known antiinflammatory and analgesic agents such as 5-aroyl-1,2-dihydro-3H-pyrrole-1-[1,2-a]pyrrolo-carboxylic acids and 3-aroyl-indol-1-ylacetic acids. See J. M. Muchoski et al., *J. Med. Chem.* 28(8), 1037(1985); and U.K. Pat. No. 1,260,868 respectively.

It was found that the same rearrangement takes place when various substituted 6-azasalicylate N,N-dialkylthiocarbamates were heated.

It is, therefore, the object of this invention to provide a novel process for the preparation of N,N-dialkyl-2-(methylthio)benzamides as useful precursor of pyrrole[1,2-a]pyrrolo-1-carboxylic acid derivatives and 3-aroyl-indol-1-ylacetic acids.

DETAILS OF THE INVENTION

This invention relates to a novel process for the preparation of a compound of formula I

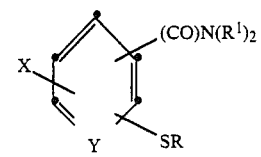

wherein X is halo, $C_{1-6}$alkyl, $C_{1-6}$alkoxy, $C_{1-6}$haloalkyl or $C_{1-6}$alkylthio; and R and $R^1$ independently are $C_{1-6}$alkyl especially methyl; and Y is C or N; with the proviso that functional groups —(CO)N($R^1$)$_2$ and —SR are adjacent to each other.

The process involves the formation of a N,N-dialkyl-thiocarbamate of formula II from a phenol of formula III followed by pyrolysis

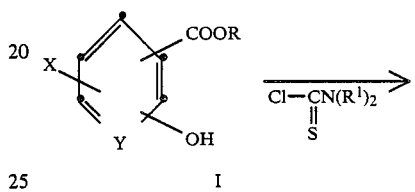

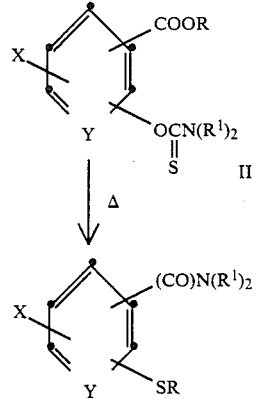

The pyrolysis is normally carried out at about 160°–300° C. preferably at 200° to 230° C. For example, methyl 5-bromo or 5-iodo salicylate N,N-dimethylthiocarbamates, upon heating, yielded the corresponding N,N-dimethyl 2-(methylthio)benzamides at temperatures below 200° C. However, in the 5-chloro or 5-fluoro series, higher temperatures were needed to effect rearrangement. No solvent should be used as it promotes the formation of thiosalicylate N,N-dialkylcarbamates. The following examples illustrates the process of this invention:

EXAMPLE

Step A: Preparation of Methyl 5-Bromosalicylate O-(N,N-dimethylthiocarbamate)

To a stirred, ice-cooled solution of 5.08 g (0.022 mol) of methyl 5-bromosalicylate in dried N,N-dimethylformamide (25 mL) was added 1.0 g of NaH (60% dispersion in mineral oil) in portions over 20 minutes. After an additional 20 min, the ice-bath was removed, the mixture allowed to stir at ambient temperatures for 1 hr, and re-cooled. 3.7 g (0.03 mol) of N,N-dimethylthiocarbamoyl chloride was then added all at once, the ice-bath removed, the mixture allowed to reach room temperature and then heated in an oil-bath set at 75° C. for 1 hr.

The cooled mixture was then added to a stirred, ice cooled mixture of ethyl ether (75 mL) and 1% NaOH solution (100 mL) in portions. The mixture was separated, the ether layer washed successively with H$_2$O, dilute HCl, water, and dried over Na$_2$SO$_4$. The wax obtained from the concentrated ether solution was triturated with isopropanol to yield the title compound as pale yellow crystals: $^1$H NMR (CDCl$_3$): δ 3.36(s, 3H), 3.42(s, 3H), 3.81(s, 3H), 6.99(d, 1H), 7.64(dd, 1H), 8.09(d, 1H); MS(EI)317/319(M+).

Step B: Preparation of N,N-Dimethyl 5-Bromo-2-(methylthio)benzamide

Methyl 5-bromosalicylate O-(N,N-dimethylthiocarbamate)(1.1 g, 0.0033 mole) is placed under a nitrogen atmosphere, stirring, and then set in an oil-bath set at 230° C. and kept at this temperature for 1.3 hr. On cooling, the oily residue is taken up in a small amount of methylene chloride and added to a 40 g silica gel column packed with the same solvent. Elution with methylene chloride followed by 10% ethyl acetate/methylene chloride yielded the title compound as an oil: $^1$H NMR(CDCl$_3$): δ 2.41(s, 3H), 2.82(s, 3H), 3.08(s, 3H), 7.14(d, 1H), 7.31(d, 1H), 7.42(dd, 1H); MS(EI)273/275(M+).

Following the same procedure as described above in Step A and Step B, there was prepared N,N-dimethyl-6-aza-2-(methylthio)benzamide (m.p. 79°-80° C.) from methyl 6-azasalicylate (methyl picolinate).

We claim:

1. A process for preparing a compound of formula I

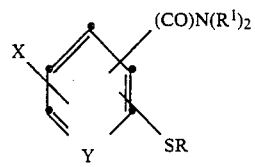

wherein X is halo, C$_{1-6}$alkyl, C$_{1-6}$aloxy, halo C$_{1-6}$alkyl or C$_{1-6}$alkylthio;

R and R$^1$ independently are C$_{1-6}$alkyl; and Y is C or N; comprising (a) treating a compound of formula III

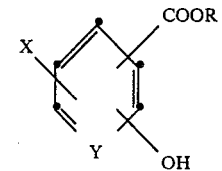

with a reagent of formula

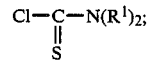

(b) heating the product from step (a) at 160°-300° C.

2. The process of claim 1 wherein the compound to be prepared is of formula I where X represents halo; R and R$^1$ are both methyl; and Y is C.

3. The process of claim 1 wherein the product from step (a) is heated at 230° C.